United States Patent [19]

Fonger et al.

[11] Patent Number: 5,171,218

[45] Date of Patent: Dec. 15, 1992

[54] BIDIRECTIONAL FEMORAL ARTERIAL CANNULA

[75] Inventors: James D. Fonger, Wayland, Mass.; Kenneth R. Jonkman, Grand Rapids, Mich.

[73] Assignees: Trustees of Boston University, Boston, Mass.; DLP, Inc., Grand Rapids, Mich.

[21] Appl. No.: 816,874

[22] Filed: Jan. 2, 1992

[51] Int. Cl.⁵ ............................................. A61M 5/178
[52] U.S. Cl. ..................................................... 604/164
[58] Field of Search ............... 604/164, 165, 167, 169, 604/170, 168, 280, 900

[56] References Cited

U.S. PATENT DOCUMENTS

| | | | |
|---|---|---|---|
| 1,879,249 | 9/1932 | Honsaker | 604/280 |
| 3,605,750 | 9/1971 | Sheridan et al. | 604/280 |
| 4,114,618 | 9/1978 | Vargas | 604/164 |
| 4,180,068 | 12/1979 | Jacobsen et al. | 604/164 |
| 4,863,441 | 9/1989 | Lindsay et al. | 604/280 |
| 4,895,564 | 1/1990 | Farrell | 604/164 |

FOREIGN PATENT DOCUMENTS 139091  5/1985  European Pat. Off. ............ 604/168

OTHER PUBLICATIONS

Clarence Dennis, M.D. et al., "Clinical Use of a Cannula for Left Heart Bypass Without Thoracotomy; Experimental Protection Against Fibrillation by Left Heart Bypass," *Annuls of Surgery*, Oct. 1962, vol. 156, No. 1, pp. 623-637.

Lynn M. Pfaender, "Hemodynamics in the Extracorporeal Aortic Cannula: Review of Factors Affecting Choice of the Appropriate Size," *The Journal of Extra-Corporeal Technology*, vol. 13; No. 4 1981, pp. 224-232.

J. Michael Duncan et al., "Rapid Placement of the Hemopump and Hemofiltration Cannula," *Ann. Thorac. Surg.*, 1990; 50:667-669.

Robert Read, M.D. et al., "Improved Cannulation Method for Extracorporeal Membrane Oxygenation," *Ann. Thorac. Surg.*, 1990; 50:670-671.

Clarence Dennis, M.D. et al., "Left Atrial Cannulation without Thoracotomy for Total Left Heart Bypass," *Acta Chir Scand*, vol. 123, 1962, pp. 267-279.

*Primary Examiner*—Mangene
*Assistant Examiner*—Thomas Price
*Attorney, Agent, or Firm*—Hamilton, Brook, Smith & Reynolds

[57] ABSTRACT

An arterial cannula which includes a diverting side hole which simultaneously perfuses blood to the body and the lower extremity. Two barbs on the cannula exterior position the diverting hole just inside the blood vessel and prevent the back wall of the blood vessel from blocking the diverting hole. A transparent flash chamber on the proximal end of the cannula provides a visual indication of the entrance of the diverting side hole into the blood vessel. When the diverting hole enters the blood vessel, blood immediately fills the flash chamber.

10 Claims, 7 Drawing Sheets

BIDIRECTIONAL FEMORAL ARTERIAL CANNULA

RELATED CO-PENDING APPLICATIONS

U.S. application Ser. No. 07/600,483, filed on Oct. 19, 1990, titled PERCUTANEOUS TRANSSEPTAL LEFT ATRIAL CANNULATION SYSTEM.

BACKGROUND OF THE INVENTION

In patients experiencing cardiopulmonary failure, a need exists to perfuse blood systemically. A femoral arterial cannula is typically used to infuse oxygenated blood into the body at the groin. To supply an adequate amount of oxygenated blood, the outer diameter of the cannula often occludes the inner diameter of the blood vessel as oxygenated blood is delivered through the lumen within the cannula. Blood exits the cannula from an opening at the distal end which typically directs blood toward the heart of the patient. For patients undergoing long-term cardiopulmonary assistance, the problem of ischemia in the lower extremity arises since the cannula blocks blood flow to the lower leg. A need exists to supply adequate blood flow to the lower leg tissues.

Prior attempts to obviate ischemia caused by arterial cannula occlusion have been awkward and inadequate. For example, the insertion of an arterial cannula in the aorta to avoid blockage has been suggested. Admittedly, the large diameter of the aorta permits the insertion of a large cannula without resulting in distal occlusion. However, such abdominal or thoracic surgery is invasive and more dangerous than the insertion of a cannula in a femoral artery. These dangers limit invasive techniques to only the most critically ill patients.

A second cannula can also be used to deliver blood to the lower leg when the femoral artery has been occluded by the systemic cannula. For example, a Y connector and tube could be inserted proximal to the occluding cannula and the distal end of the tube fitted with a catheter which is inserted into the femoral artery distal to the cannula. This also requires extra hardware and another cannulation.

SUMMARY OF THE INVENTION

A longstanding need exists for a bidirectional femoral arterial cannula which will deliver blood in both directions to maintain an adequate flow to the heart as well as in the direction of the lower extremity. The femoral arterial cannula of the invention achieves this bidirectional flow by means of a small diverting hole in the side of the cannula. The cannula comprises a first tube including a proximal end, a distal tip with an opening, a diverting side hole, and a barb on the tube exterior to position the diverting side hole away from the wall of the blood vessel such that fluid flowing in the first tube exits the distal tip opening in a first direction and exits the diverting side hole in a second direction. For example, blood is infused in the direction of the lower extremity through the diverting side hole and in the direction of the heart and body through the distal tip opening. The tube can be radiopaque to assist in positioning. However, the cannula can be properly positioned without resorting to fluoroscopic techniques. A cannula wall barb is positioned adjacent the diverting side hole. The barb permits the diverting side hole to be properly positioned in the blood vessel so as not to be occluded by the blood vessel wall. The proximal face of the barb has a steep slope which abuts the inner wall of the blood vessel and prevents the diverting side hole from occluding. The distal facing portion of the barb has a shallow slope which facilitates insertion of the barb into the blood vessel percutaneously over a guide wire.

The cannula further comprises a hub assembly connected to the proximal end of the first tube. The hub assembly includes a transparent flexible hub such that when the diverting side hole enters the blood vessel, blood flows into the hub region and provides a visual indication of the entry of the diverting side hole into the blood vessel. The cannula invention also includes a dilator assembly which is positioned inside the first tube. The dilator assembly is comprised of a distal end with a diameter which occludes the distal opening of the first tube. The proximal end of the dilator has a smaller diameter and serves as an obturator which stiffens the dilator assembly. The dilator assembly also includes a dilator hub which inserts into the hub assembly of the first tube such that a hollow passage is formed between the first and second tubes which allows blood from the diverting side hole to flow into the transparent hub assembly region. The dilator assembly further includes a guide wire channel within the second tube which allows for percutaneous insertion of the bidirectional cannula. As noted previously, the hollow passage serves as a flash chamber which provides a visual indication of when the diverting side hole enters the blood vessel. The hub assembly also includes a flange which can be used to fasten the entire cannula assembly to the patient's skin.

The addition of a diverting side hole, barb, and a hollow flash chamber for a visual indication of the entrance of the diverting side hole affords easy percutaneous insertion and proper placement of the bidirectional cannula in a femoral artery. The cannula is inserted into the femoral artery until the diverting side hole is inside of the blood vessel. At this point, blood flows into the transparent passage and flash chamber between the first and second tubes. This provides a positive visual indication to the physician that the diverting side hole is adequately within the blood vessel. The dilator assembly is then withdrawn and the proximal end of the cannula attached to a pump circuit. Thus, the distal end opening of the cannula provides systemic blood flow to the body while the diverting side hole provides blood flow to the leg. Ischemia and possible necrosis are thus avoided in patients undergoing extended cardiopulmonary assistance.

The above and other features of the invention including various novel details of construction and combinations of parts will now be more particularly described with reference to the accompanying drawings and pointed out in the claims. It will be understood that the particular device embodying the invention is shown by way of illustration only and not as a limitation of the invention. The principles and features of this invention may be employed in varied and numerous embodiments without departing from the scope of the invention.

DETAILED DESCRIPTION OF THE INVENTION

Figure 1:
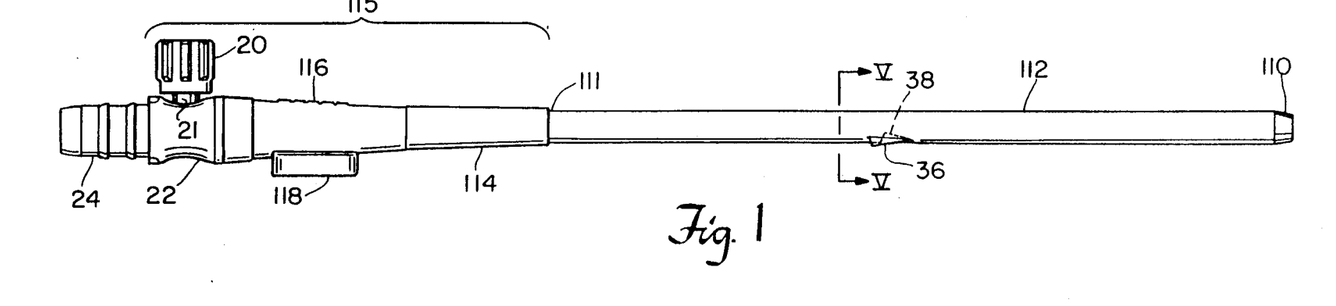
FIG. 1 shows a side view of the cannula of the invention.
Figure 5:
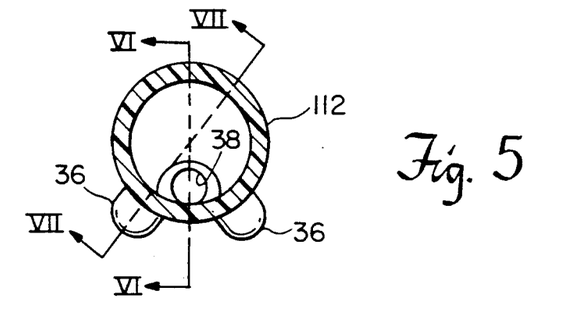
FIG. 5 shows a cross-sectional view of the cannula of FIG. 1.
Figure 6:
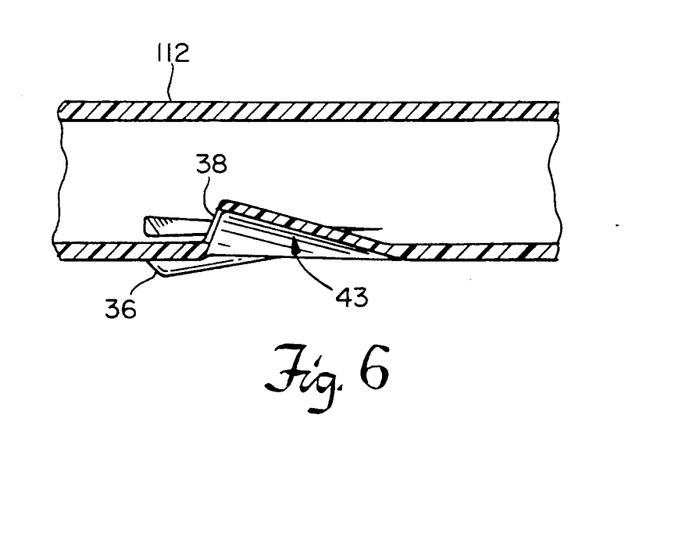
FIG. 6 illustrates a longitudinal cross-sectional view of the cannula which encompasses the diverting side hole.
Figure 7:
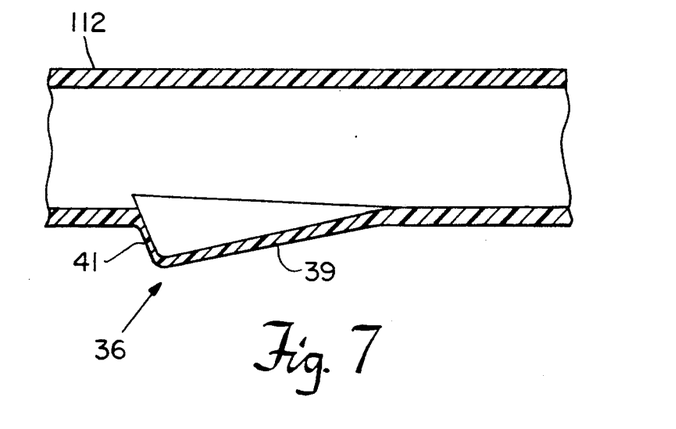
FIG. 7 illustrates a longitudinal cross-sectional view of the cannula which encompasses the protuberances.

To prevent lower extremity ischemia and resulting tissue necrosis, the cannula of the invention supplies blood to both the body as well as in the opposite direction to the leg. FIG. 1 illustrates the simple construction of the bidirectional femoral arterial cannula. The cannula is comprised of a radiopaque polyurethane thin wall tube 112, with an outer diameter of 6 mm, which includes a tapered tip 110 with an opening for supplying blood to the main body of the patient. Tip 110 has an inner diameter of 4 mm and an outer diameter of 5 mm. Tube 112 can be typically 17 French or 14 French in width or other desired sizes as well. FIGS. 5, 6, and 7 illustrate the diverting side hole 38 for supplying blood to the lower extremity of the patient, and barb 36 for positioning the cannula diverting side hole within the blood vessel without blood vessel wall occlusion.

Figure 8:
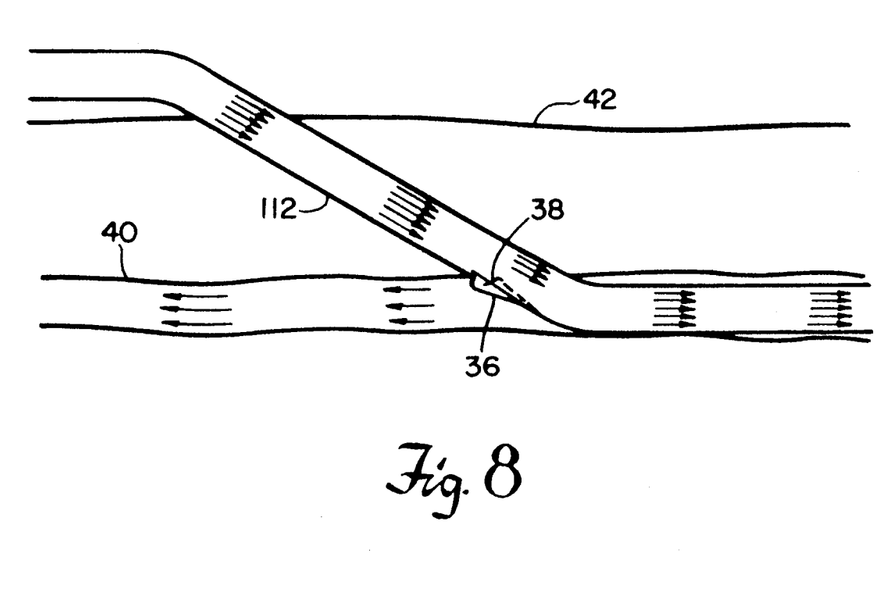
FIG. 8 illustrates the operation of the cannula of the invention after the dilator assembly has been withdrawn and a blood pump attached.

As shown in FIG. 7, barb 36 comprises a distal facing portion 39 with a shallow slope and a proximal facing portion 41 with a steep slope. The shallow slope of barb portion 39 facilitates insertion of the cannula into the artery. The steep slope of barb portion 42 abuts the inner wall of the blood vessel and properly positions the diverting side hole 38. Barb 36 is 1 cm in length and 1 mm in height. FIG. 5 illustrates the symmetrical placement of barbs 36, 5 mm apart, on either side of diverting side hole 38, which is located in a depression 43 on the exterior of the wall of cannula 112 and is 2 mm in diameter. As shown in FIG. 6, diverting side hole 38 is slanted with respect to the wall of cannula 112 and is less likely to be occluded in that position. FIG. 8 illustrates the placement of the cannula of the invention in a blood vessel for long term cardio-pulmonary patient support.

Figure 2:
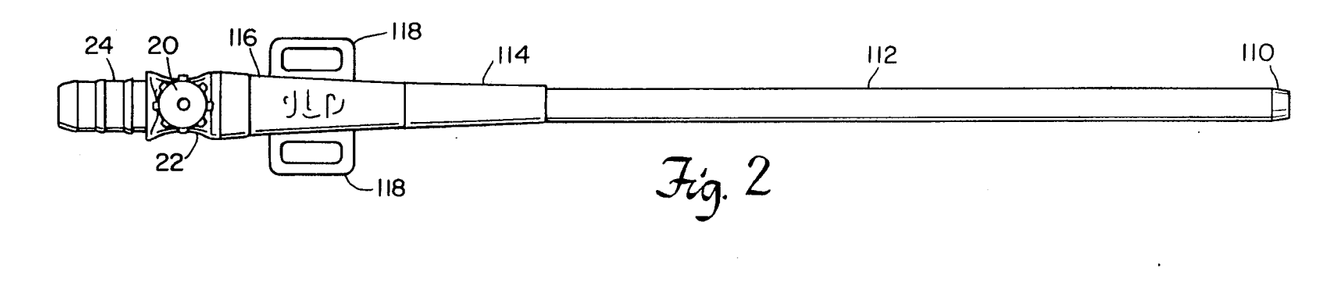
FIG. 2 shows a top view of the cannula of the invention.

The proximal end 111 of cannula 112 is attached to a polyvinylchloride hub assembly 115. Hub assembly 115 includes a transparent flexible hub in segments 114, 116, and 22. As shown in FIG. 1, barb 36 is located 9 cm from tip 110 and 8.5 cm from hub 115. A short hub segment 114 is 1.5 cm in length. Hub segment 116 has a clamp area which is 3.5 cm in length extends from flange 118 to hub segment 114. As will be shown below, the transparent hub provides a visual indication of the entry of the diverting side hole into the blood vessel. The hub is connected to a rigid barbed connector 24 which can be coupled to standard ⅜" tubing. The hub also includes an air bleed inlet 2 with a screwable cap 20 which permits adjustment of the opening. Flanges 118 allow the hub assembly to be sewn or clamped onto the patient's skin and prevent unwanted movement of the cannula. Flanges 118 are shown in more detail in the top view of FIG. 2.

Figure 3:
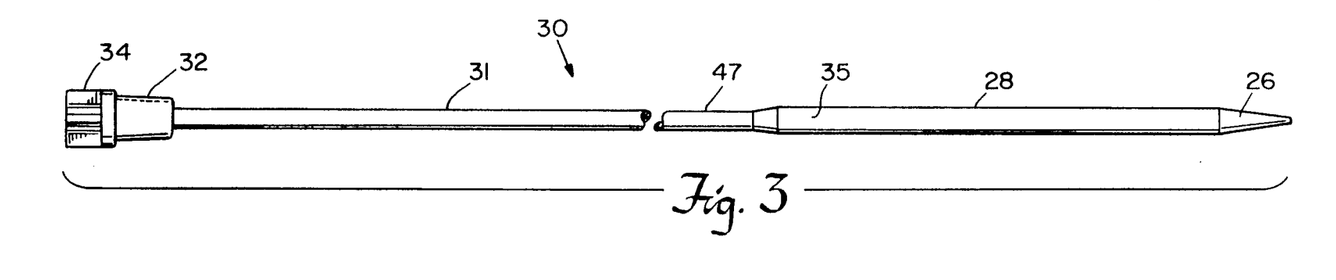
FIG. 3 illustrates the dilator assembly of the cannula of the invention.

Dilator assembly 30 of FIG. 3 serves as an obturator or stiffener and is inserted into the interior of the cannula 112 and its associated hub assembly 115. The dilator assembly includes a second polyurethane tube 31 with a distal end 28, 9 cm in length, with a first diameter of 4 mm which occludes the first tube distal tip opening. The thickened portion of distal end 28 is 7.5 cm in length. Tapered tip 26 on second tube 31 facilitates insertion of the dilator assembly into the first tube of the cannula and dilates the guide wire hole in the vessel for cannula introduction. A polypropylene dilator hub with a tapered portion 32 seals inside of the rigid barbed connector 24 of hub assembly 115 and outer hub 34 is a handle for manipulation of the dilator. Portion 47 of second tube 31 is 20.5 cm in length and has a second diameter of 3 mm which is less than the first diameter. Thus, a hollow flash chamber is formed between the first and second tubes which allows blood entering the diverting side hole to flow into the hub assembly region. This provides the physician with a visual indication that the diverting side hole has entered the blood vessel. Only blood from the diverting side hole 38 can enter the flash chamber because the distal end 28 of second tube 31 occludes the distal end 110 of cannula 112. A guide wire 35 can also be introduced inside of the second tube 31 to guide the insertion of the cannula into the blood vessel.

Figure 4A:
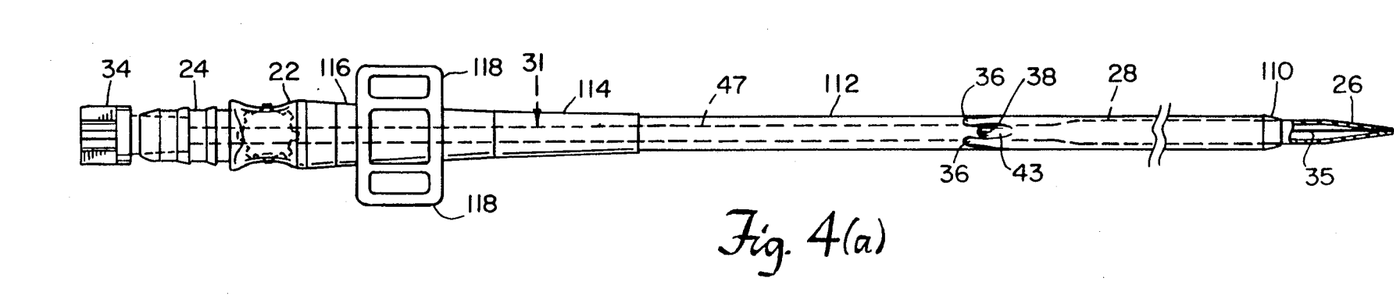
FIG. 4(a) shows the combined cannula and dilator assembly of the invention.
Figure 4B:
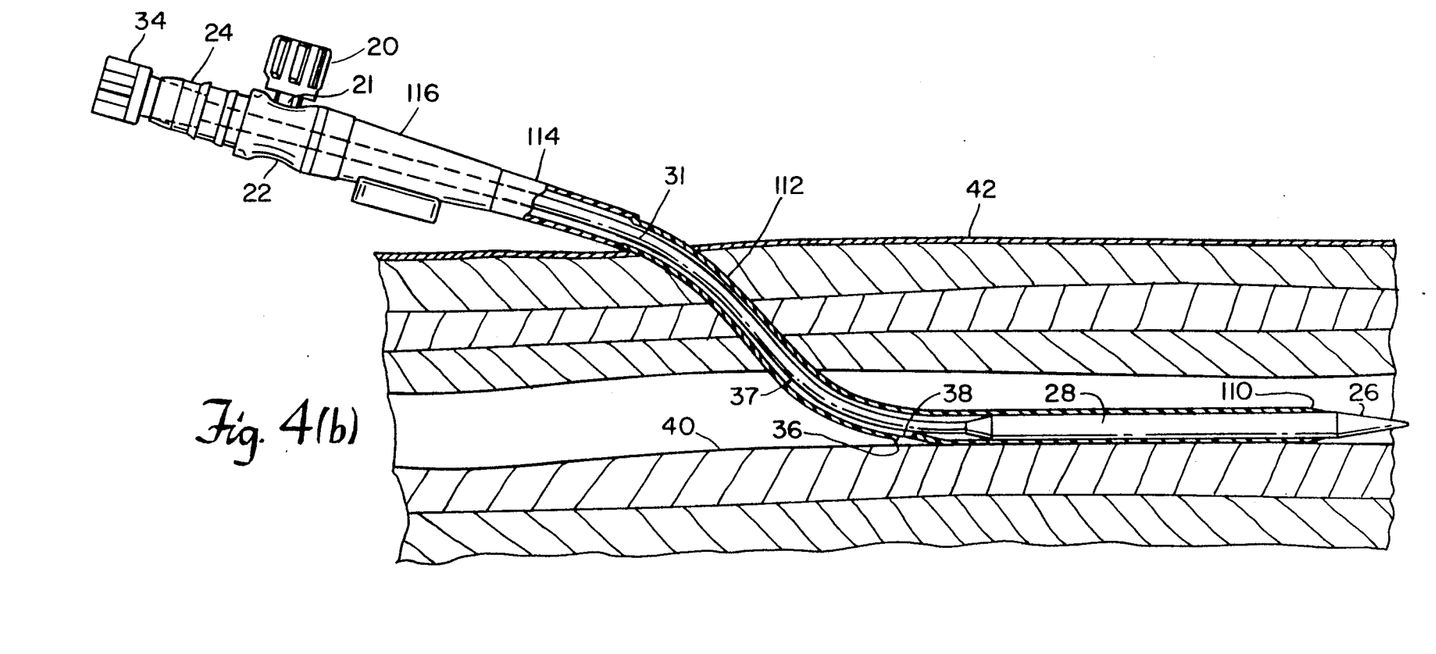
FIG. 4(b) illustrates the initial placement of the cannula of the invention in a femoral artery and the operation of the visual indicators of the cannula.

The assembled cannula is shown in FIG. 4(a). FIG. 4(b) illustrates the operation of the visual indicator during the insertion of the cannula into the blood vessel. The diverting side hole 38 is shown resting on the wall of the blood vessel 40. Diverting side hole 38 is 1.5 cm from the thickened portion of distal end 28 of second tube 31. In this position, blood will fill the hollow chamber 37 between first tube 112 and second tube 31. The blood will flow into the transparent hub region and provide the physician with a visual indication of proper placement. The second tube 31 of dilator assembly 30 can also be of radiopaque plastic.

FIG. 4(b) also illustrates the placement of the cannula of the invention using barb 36 and diverting side hole 38. Skin 42 in the groin region is pierced using a conventional Seldinger needle. Tapered tip 26 on second tube 31 facilitates the dilation of the blood vessel. Cannula wall 112 is threaded into blood vessel 40 until the diverting side hole 38 enters the blood vessel. As noted previously, blood enters diverting side hole 38 and provides a visual indication in the area of the transparent hub as blood flows into hollow chamber 37. The dilator assembly also serves as an obturator or stiffener to assist in the introduction of the cannula. With air bleed hole 21 open, blood can easily flow into the flash chamber 37. The dilator assembly is then removed and rigid barb connector 24 is hooked up to standard ⅜" tubing connected to a blood pump circuit. The hub segment 116 is clamped after the dilatory assembly is removed. Once connector is attached to the blood pump tubing, the clamp can be removed from hub segment 116.

The bidirectional cannula of the invention provides adequate distal perfusion of the cannulated lower extremity. Thus, extended cardiopulmonary assistance can be provided with a greatly reduced risk of ischemia to the lower limb. The cannula of the invention can be used with any assist circuit. For example, the device could be attached to a percutaneous transseptal left atrial cannulation system. It can also be used for extracorporeal membrane oxygenation where heart function is adequate, but the lungs are failing. Any type of blood pump can be used with the cannula of the invention to provide a closed vascular circuit.

Figure 9:
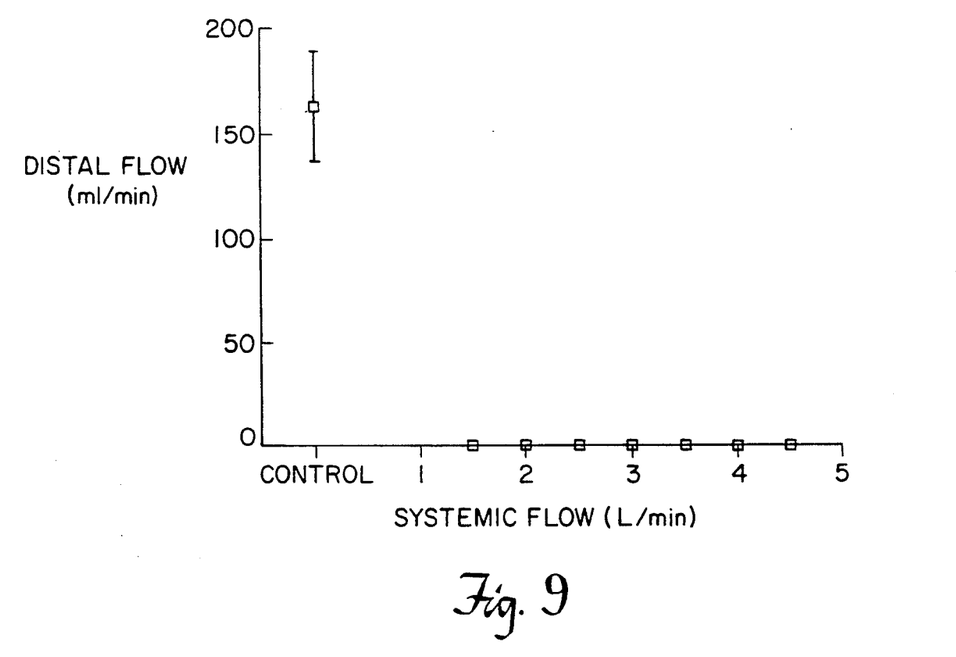
FIG. 9 illustrates the distal flow output of a conventional unidirectional cannula.
Figure 10:
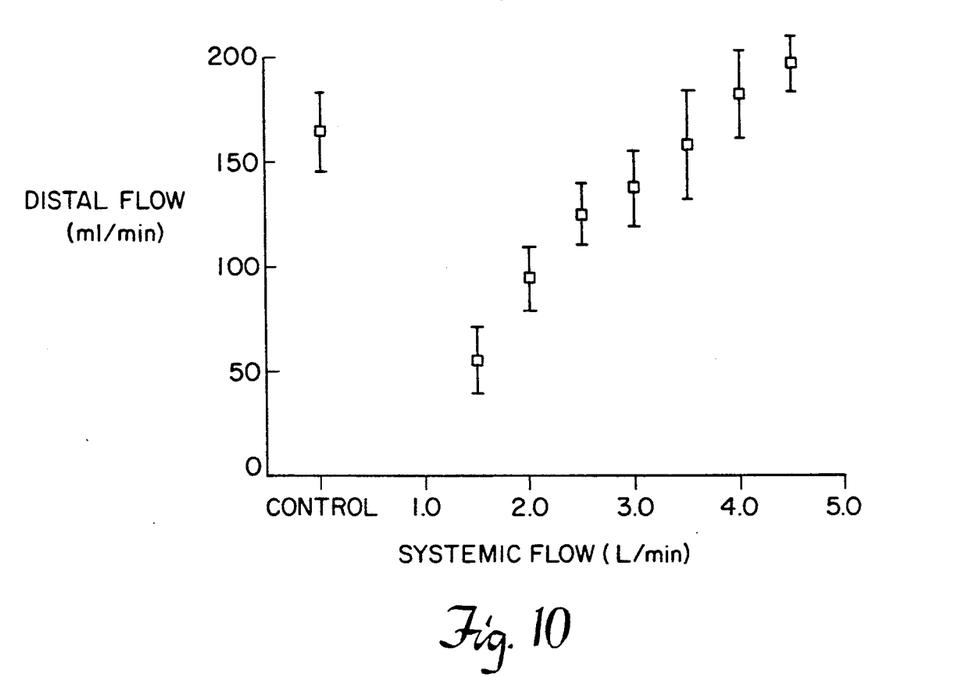
FIG. 10 illustrates the distal flow of the bidirectional cannula of the invention.

FIGS. 9-14 show the experimental data which illustrates the ability of the cannula of the invention to maximize pressure, flow, and oxygenation in the cannulated lower extremity. Experiments were performed on 200 pound pigs in which a conventional unidirectional cannula was inserted in one femoral artery and the bidirectional cannula of the invention was inserted in the other femoral artery. Flow probes and pressure catheters were positioned distal to the respective cannulae and measurements were taken over a spectrum of pump flows. Control values are with the pump turned off and before the cannulae are inserted into the femoral artery. FIG. 9 illustrates the distal flow in an extremity in which a conventional unidirectional cannula has been placed. As can be seen from FIG. 9, distal flow is nonexistent in the lower extremity at all levels of perfusion. However, as shown in FIG. 10, when the bidirectional cannula of the invention is used, distal blood flow exceeds control values at full pump flow.

Figure 11:
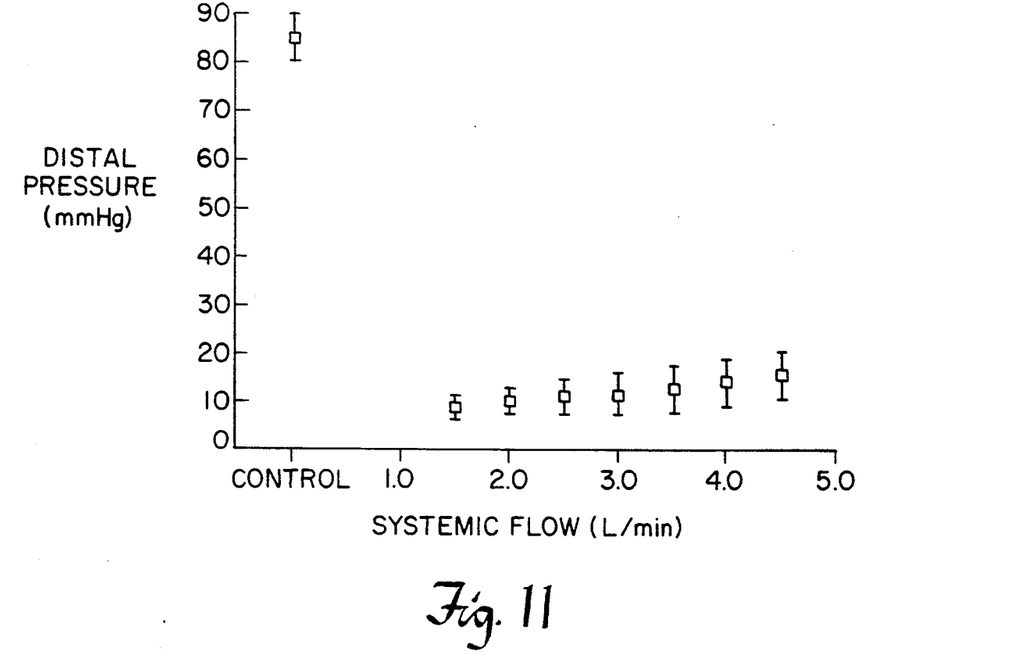
FIG. 11 illustrates the distal pressure output of a conventional unidirectional cannula.
Figure 12:
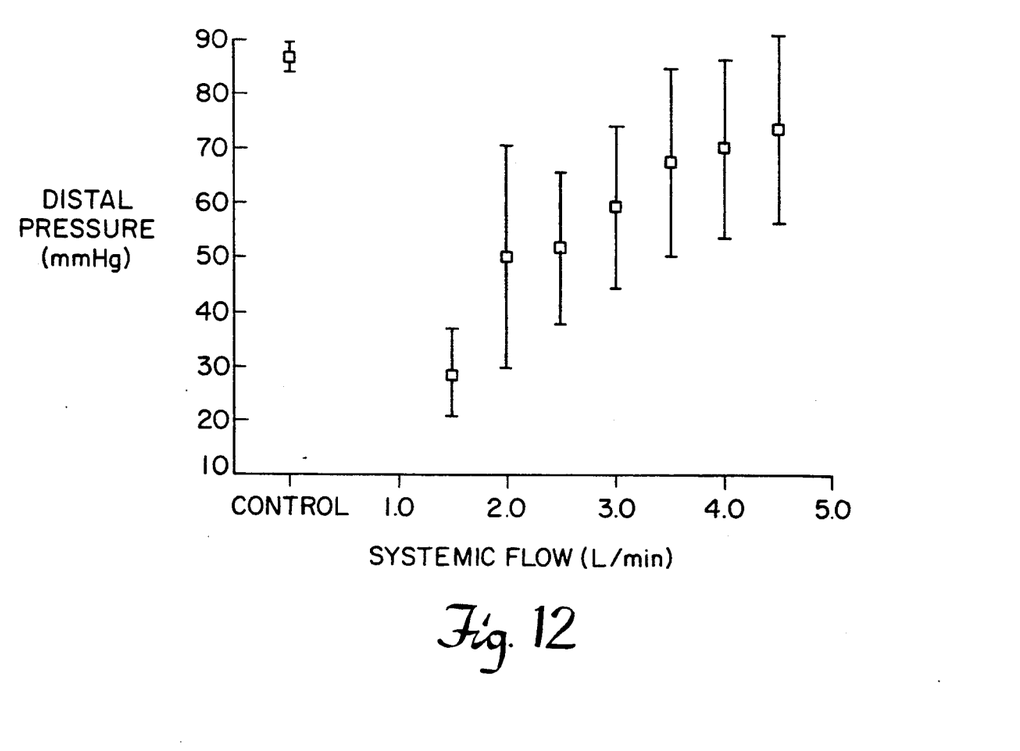
FIG. 12 illustrates the distal pressure output of a bidirectional cannula of the cannula.

Similar data is produced when distal pressure is measured. For example, FIG. 11 illustrates the distal pressure associated the conventional unidirectional cannulation. Blood pressure is minimal even at high flows in the lower extremity. However, when a bidirectional cannula of the invention is used, blood pressure approaches the control value at full flow.

Figure 13:
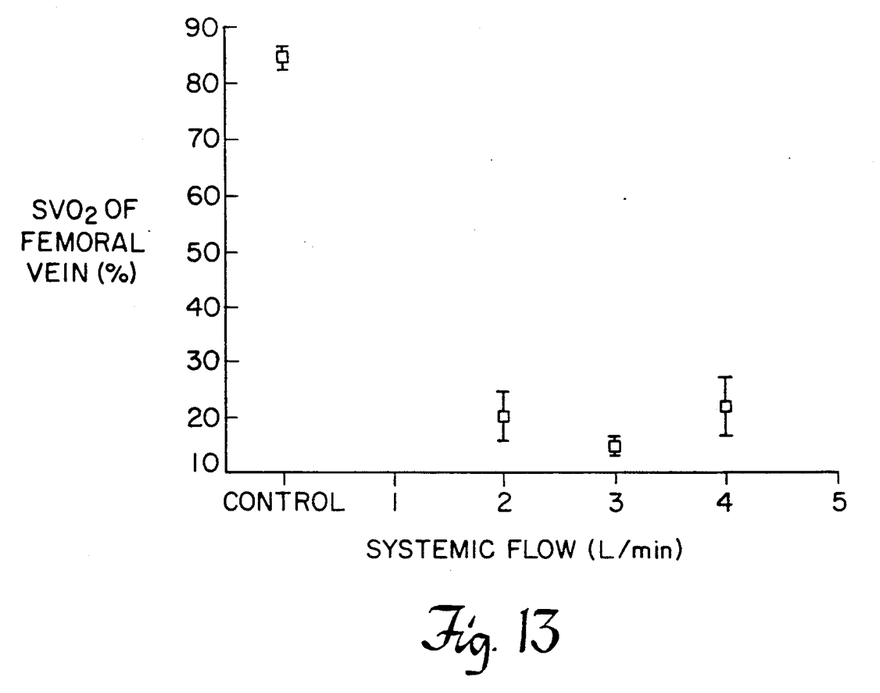
FIG. 13 illustrates the mixed venous oxygen saturation ($SVO_2$) of a conventional unidirectional cannula.
Figure 14:
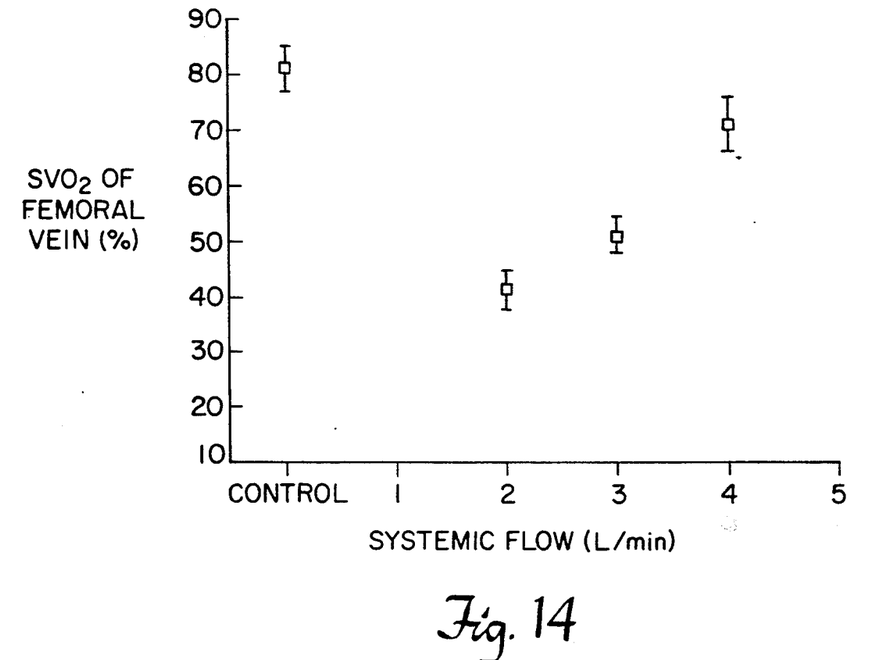
FIG. 14 illustrates the mixed venous oxygen saturation ($SVO_2$) of the bidirectional cannula of the invention.

Finally, the mixed venous oxygen saturation (SVO$_2$) was measured as an index of total limb perfusion, both directly from the cannula and also from native collateral vessels. Low SVO$_2$ indicates poor perfusion and with a unidirectional cannula in place it indicates that collateral flow contributes very little to overall limb perfusion. Conversely, high SVO$_2$ indicates good limb perfusion. The unidirectional cannula in FIG. 13 is associated with minimal direct or collateral flow whereas the bidirectional cannula in FIG. 14 produces almost a nominal SVO$_2$ at high flows.

The bidirectional femoral arterial cannula of the invention provides adequate flow to the limb in cardiopulmonary assistance circuits used for long term applications. The barbed diverting side hole and blood flash chamber are simple to construct and easy to insert into the patient. Thus, a safe long term method for femoral artery cannulation is provided with minimal risk to the patient. Positioning can be accomplished percutaneously without resort to direct surgical exposure or fluoroscopic techniques because of the visual and tactile indications provided to the surgeon by the device.

EQUIVALENTS

Those skilled in the art will recognize, or be able to ascertain, using no more than routine experimentation, many equivalents to the specific embodiments of the invention described herein. These and all other equivalents are intended to be encompassed by the following claims.

We claim:

1. A bidirectional cannula comprising a first tube including:
   (i) a proximal end;
   (ii) a distal tip with an opening;
   (iii) a diverting side hole; and
   (iv) at least one barb on the tube exterior for positioning the diverting said hole away from the wall of the blood vessel such that fluid flowing in the first tube exits the distal tip opening in a first direction and exits the diverting side hole in a second direction opposite of the first direction, the diverting side hole being formed in a depression in the first tube for diverging fluid flow in the second direction.

2. A cannula, as recited in claim 1, wherein the tube is radiopaque.

3. A cannula, as recited in claim 1, wherein the first tube further comprises a first barb and a second barb which are positioned adjacent the diverting side hole.

4. A cannula, as recited in claim 3, wherein the diverting side hole is positioned in a depression in the tube exterior between the first and second barbs.

5. A cannula, as recited in claim 1, further comprising a hub assembly connected to the proximal end of the first tube, said hub assembly including a transparent flexible hub such that when the diverting side hole enters the blood vessel, blood flows into the hub region and provides a visual indication of the proper placement of the diverting side hole.

6. A cannula, as recited in claim 5, further comprising:
   a dilator assembly which is positioned inside of the first tube, including:
   (i) a second tube having a distal end with a first diameter which occludes the first tube distal tip opening and a proximal end with a second diameter which is less than the first diameter, and
   (ii) a dilator hub which is connected to the hub assembly and the proximal end of said second tube such that a hollow passage is formed between the first and second tubes which allows blood entering the diverting side hole to flow into the hub assembly region.

7. A cannula, as recited in claim 1, wherein the barb further comprises:
   a) a distal facing portion with a shallow slope which facilitates insertion of the cannula into a blood vessel, and
   b) a proximal facing portion with a steep slope which may abut the inner wall of the blood vessel and prevent inadvertent extraction of the diverting side hole outside of the vessel.

8. A method of positioning a bidirectional cannula in a blood vessel comprising the steps of:
   (1) forming a tube including a transparent proximal end, a distal tip with an occluded opening, a diverting side hole, and a barb adjacent to the diverting side hole;
   (2) inserting the tube distal tip into the blood vessel until the diverting side hole is inside of the blood vessel and blood is flowing into the transparent proximal end of the tube; and
   (3) directing the blood continuously in a first direction through the distal tip and in a second direction opposite to the first direction through the diverting side hole.

9. A bidirectional cannula, for insertion into a blood vessel wall, comprising
(a) a first tube including
  (i) a proximal end;
  (ii) a distal tip with an opening;
  (iii) a diverting side hole; and
  (iv) at least one barb on the tube exterior to position the diverting side hole away from the blood vessel wall such that fluid flowing in the first tube exits the distal tip opening in a first direction and exits the diverting side hole in a second direction;
(b) a hub assembly including:
  (i) a transparent flexible hub coupled to the first tube proximal end;
  (ii) a rigid barbed connector coupled to said hub;
  (iii) an air bleed hole connected to said hub; and
  (iv) a flange, connected to the hub, for fixing the hub assembly;
(c) a dilator assembly, which is positioned inside of the first tube, including:
  (i) a second tube having a distal end with a first diameter which occludes the first tube distal tip opening and a proximal end with a second diameter which is less than the first diameter, within the
  (ii) a dilator hub which fits w hub assembly and into the proximal end of the second tube such that a hollow passage is formed between the first tube and the second tube which allows blood entering the diverting side hole to flow into the hub assembly region;
  (iii) a guide wire lumen in the second tube interior; and
  (iv) a guide wire in the second tube lumen.

10. A bidirectional cannula comprising:
a first tube including:
  (i) a proximal end;
  (ii) a distal tip with an opening;
  (iii) a diverting side hole;
  (iv) at least one barb on the tube exterior to position the diverting side hole away from the wall of the blood vessel such that fluid flowing in the first tube exits the distal tip opening in a first direction and exits the diverting side hole in a second direction; and hole in a second direction; and
a hub assembly connected to the proximal end of the first tube, said hub assembly including a transparent flexible hub such that when the diverting side hole enters the blood vessel, blood flows into the hub region and provides a visual indication of the proper placement of the diverting side hole.

* * * * *

UNITED STATES PATENT AND TRADEMARK OFFICE
CERTIFICATE OF CORRECTION

PATENT NO.    : 5,171,218
DATED         : December 15, 1992
INVENTOR(S)   : James D. Fonger and Kenneth R. Jonkman It is certified that error appears in the above-identified patent and that said Letters Patent is hereby corrected as shown below:

Claim 1, column 6, line 11, change "said" to --side--, and in line 17, change "diverging" to --diverting--.

Claim 9, column 7, lines 27 and 28, delete "within the" and in Column 8, line 1, change "w" to --within the--.

Claim 10, column 8, line 21, delete "hole in a second direction; and."

Signed and Sealed this

Twenty-sixth Day of October, 1993

Attest:

BRUCE LEHMAN

Attesting Officer            Commissioner of Patents and Trademarks